(12) United States Patent
Kautzer et al.

(10) Patent No.: US 7,330,529 B2
(45) Date of Patent: Feb. 12, 2008

(54) STATIONARY TOMOGRAPHIC MAMMOGRAPHY SYSTEM

(75) Inventors: Jeffrey Alan Kautzer, Pewaukee, WI (US); Christopher David Unger, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 113 days.

(21) Appl. No.: 10/708,999

(22) Filed: Apr. 6, 2004

(65) Prior Publication Data

US 2005/0226371 A1 Oct. 13, 2005

(51) Int. Cl.
*A61B 6/04* (2006.01)
(52) U.S. Cl. ............................................ 378/37; 378/25
(58) Field of Classification Search ................ 378/37, 378/119, 200, 146, 12, 193–198, 41–45, 10, 378/21–27, 9, 92, 57
See application file for complete search history.

(56) References Cited

U.S. PATENT DOCUMENTS

| | | | |
|---|---|---|---|
| 5,729,583 A | | 3/1998 | Tang et al. |
| 5,761,269 A | * | 6/1998 | Sugihara et al. ............ 378/199 |
| 6,148,061 A | | 11/2000 | Shefer et al. |
| 6,236,709 B1 | * | 5/2001 | Perry et al. .................... 378/57 |
| 6,292,531 B1 | * | 9/2001 | Hsieh ........................... 378/37 |
| 6,335,968 B1 | | 1/2002 | Malik |
| 6,480,566 B2 | | 11/2002 | Muller et al. |
| 6,553,096 B1 | | 4/2003 | Zhou et al. |
| 6,760,407 B2 | | 7/2004 | Price et al. |
| 6,807,348 B2 | * | 10/2004 | Lu et al. ...................... 385/125 |
| 6,912,268 B2 | | 6/2005 | Price et al. |
| 6,914,959 B2 | * | 7/2005 | Bailey et al. .................. 378/65 |
| 6,931,092 B2 | * | 8/2005 | Joshi et al. .................... 378/19 |
| 6,980,625 B2 | | 12/2005 | Kieffer et al. |
| 2002/0094064 A1 | | 7/2002 | Zhou et al. |

\* cited by examiner

*Primary Examiner*—Hoon Song
(74) *Attorney, Agent, or Firm*—Peter Vogel

(57) ABSTRACT

A mammography scanning system having a detector includes an arc-shaped support system having a number of X-ray emitters coupled thereto. The X-ray emitters generate a plurality of X-ray fluxes towards a common focus at varying angles with respect to the focus. Also, each of the X-ray emitters is collimated to view an entire detector field of view.

4 Claims, 1 Drawing Sheet

STATIONARY TOMOGRAPHIC MAMMOGRAPHY SYSTEM

BACKGROUND OF INVENTION

The present invention relates generally to X-ray imaging machines, and particularly to a stationary tomographic mammography system.

A traditional X-ray imaging system includes an X-ray source and a detector array for generating an internal image of an object. As is well known, the X-ray source generates X-rays, which are attenuated by the object (i.e. they either pass through the object or are absorbed therein). As a result, the transmitted X-rays vary in intensity. The detector array receives and measures the resultant X-ray flux so as to generate electrical signals necessary for constructing an internal image of the object.

In at least one known mammography imaging system, an X-ray source projects a fan-shaped beam, which is collimated to lie within an X-Y plane of a Cartesian coordinate system and is generally referred to as the "imaging plane." The X-ray beam passes through the object being imaged, such as a patient's breast. The beam, after being attenuated by the object, impinges upon an array of radiation detectors. The intensity of the attenuated beam radiation received at the detector array is dependent upon the attenuation of the X-ray beam by the object. Each detector element of the array generates a separate electrical signal that is a measurement of the beam attenuation at the detector location. The attenuation measurements from all the detectors are acquired separately to generate a transmission profile or detector signals.

Conventional film and digital detector mammography systems traditionally utilize mount mechanisms, which allow the user to manually or robotically pivot an X-ray source. This pivoting allows generation of different projection views during imaging of an individual patient breast. During this operation, the patient breasts are held by a breast compression system, which remains stationary during X-ray source movements.

In certain digital mammographic applications, such as tomography, a series of images is rapidly acquired through a sweep of projection angles, which may include 60° or more. The images are taken quickly to minimize anatomical movement and patient compression time.

However, the mechanical motion required to move the X-ray source may induce image motion artifacts and may also require sub-optimal trade-offs between X-ray source arm acceleration mechanics and overall system ergonomics.

Special considerations are currently implemented to avoid patient and operator collisions when an X-ray source, mounted on a robotic arm, is operated. In contrast, if the X-ray source is manually moved to each projection angle, the patient may sustain extended compression times, which may be undesireable. In addition, certain rapid multi-view applications may require that the X-ray source be completely stationary during the actual exposure thereby necessitating acceleration and deceleration of the angular movement.

Because very sensitive flat panel X-detectors are often utilized in such systems, it is also known that even moderate levels of shock and vibration applied to their panel read-out interconnection systems may cause image artifacts to be generated. In addition, the servo motor used to move the X-ray source to the required angles must not cause any appreciable magnetic fields to be induced into the sensitive X-ray detector or additional artifacts may be generated.

The disadvantages associated with current imaging systems have made it apparent that a new technique for mammographic imaging is needed. The new technique should minimize vibration and scan time. The present invention is directed to these ends.

SUMMARY OF INVENTION

According to one aspect of the present invention, a scanning system includes an arc-shaped support system coupled to a mount. Coupled to the arc-shaped support system is a plurality of stationary X-ray sources generating X-ray fluxes, which pass through an object (e.g. a patient). Coupled to the mount is an X-ray detector, which generates a detector signal in response to the X-ray fluxes.

According to another aspect of the present invention, a mammography scanning system having a detector includes the arc-shaped support system. The system further includes a plurality of X-ray emitters adapted to generate a plurality of X-ray fluxes. The plurality of X-ray emitters are coupled to the arc-shaped support system and are directed towards a common focus at varying angles with respect to the focus, wherein each of the plurality of X-ray emitters is collimated to view an entire detector field of view.

One advantage of the present invention is that motion free tomographic or multi-projection imaging eliminates mechanically induced artifacts in the sensitive detection system.

Another advantage of the present invention is that this type of system eliminates the shock and vibration translated from the mount to detector during the detector read, which may be conducted during mount movement.

Other advantages of the present invention will become apparent upon reading the following detailed description and appended claims and upon reference to the accompanying drawings.

BRIEF DESCRIPTION OF DRAWINGS

For a more complete understanding of this invention, reference should now be had to the embodiments illustrated in greater detail in the accompanying drawings and described below by way of examples of the invention. In the drawings.

DETAILED DESCRIPTION

The present invention is illustrated with respect to a scanning system 10 particularly suited to the medical field. The present invention is, however, applicable to various other scanning systems utilized in a variety of other environments, as will be understood by one skilled in the art.

Figure 1:
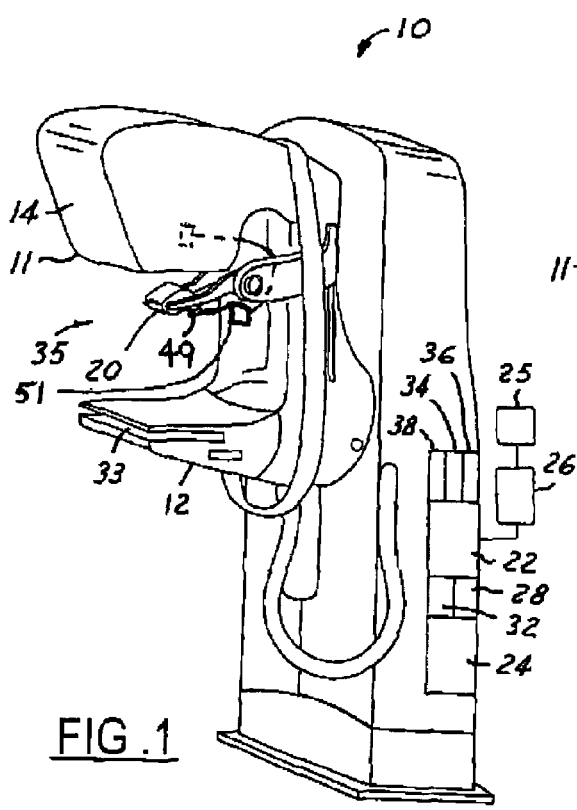
FIG. 1 is a perspective view of a mammography scanning system according to one embodiment of the present invention.
Figure 2:
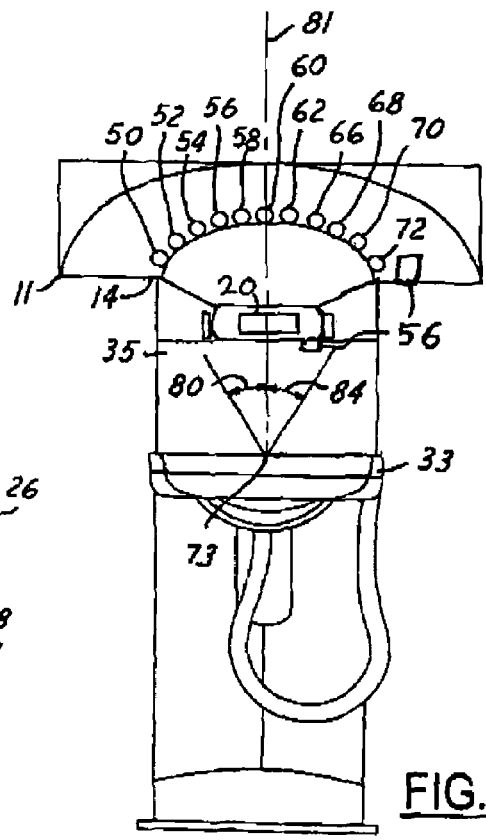
FIG. 2 is a front view of FIG. 1.

Referring to FIGS. 1 and 2, a scanning system 10 including a support system 11 coupled to a mount 12, in accordance with one embodiment of the present invention, is illustrated. Coupled to the support system 11 is a plurality of stationary X-ray sources 14 generating X-ray fluxes, which pass through an object (e.g. a patient). Also coupled to the mount 12 is an X-ray detector 20, which generates a detector signal in response to the X-ray fluxes.

The system 10 further includes a control unit 22, coupled to a host computer 24 and display 26 and various other widely known control and display components, receiving the detector signal and responding by generating an image signal. The control unit 22 includes, for example, an operator console 25, an X-ray controller 28, a compression controller 30, a mount motor controller 32, a mass storage unit 34, an image reconstructor 36 and a data acquisition system 38, all of which will be discussed later.

The mount 12 holds the support system 11, which may be coupled to a platform 33 that moves either the X-ray sources 14 or alternately the detector 20 in response to signals from the mount motor controller 32, as will be understood by one skilled in the art. The platform is embodied as planar but may also be embodied as hemispherical, cubicle, linear, or irregular in shape. In the present embodiment, the X-ray sources 14 and detector 20 are coupled to the mount 12. The mount 12 may also include a holding area 35 for supporting patient tissue.

The support system 11 is embodied as arc-shaped; however, numerous other configurations for the support system, such as hemispherical, cubicle, linear, or irregular are also embodied herein. Important to not, however is that the sources 14 do not need to be in a plane, they can also be configured at various heights into and out of a given plane.

The X-ray detector 20, which includes several detector modules, is typically located opposite the X-ray sources 14 to receive the X-ray fluxes generated therefrom. Each module shares information with other modules corresponding to a number of slices. The stationary target detector 20 may be cooled by direct liquid cooling to enable higher X-ray outputs. This liquid cooling may be controlled by a cooling system 49. In alternate embodiments of the present invention, the system 10 may include a common conditioner 51 for the tube and the detector 20, and there may be multiple coolers (i.e. multiole chillers 56).

In one embodiment of the invention, the X-ray sources 14 (emission array) include a plurality of stationary X-ray sources 50-72 (emitters) in place of conventional X-ray tube technology, which allow acquisition of a series of images at various projection angles without the mechanical motion associated with current systems.

The sources 50-72 are embodied as coupled to the support system 11 in an arc arrangement relative to the detector 20 and toward a common focus 73; however, numerous other arrangements are also embodied in the present invention. Such other embodiments include the sources 50-72 arranged directly on the mount 12 or a flat support system whereon the sources 50-72 are angled towards the detector 20, etc.

The sources 50-72 include a first source 50 at a first array angle 80 from an axis 81 perpendicular to the detector 20, generating a first X-ray flux. The sources 50-72 further include an nth source 72 at an nth array angle 84 from the axis 81 perpendicular to the detector 20. The other sources 52-70 are also positioned at various angles relative to the axis 81 perpendicular to the detector 20 and generate various X-ray fluxes. Important to note is that any of the sources 52-72 may be considered a second source or a third source etc., wherein the first source 50 may also be positioned at any angle with respect to the axis 81 perpendicular to the detector 20.

Rather than mechanically sweep the single source tube, the array of X-ray sources 50-72 in an arc 90 above the detector 20 scans the object. Each emitter is collimated to view the entire detector field of view (FOV). The emitters are fired sequentially or simultaneously and the detector 20 is read after each emission by the host computer 24.

In one embodiment of the invention, the X-ray sources 14 (emission array) are capable of projecting the required X-ray flux at each tomographic application angle required and thus eliminate need for mechanical movement of an X-ray source.

In other embodiments, the angle through which the prior art X-ray source must be mechanically swept can be reduced using an array 14, which offers a number of emission flux angles but not necessarily all the angles required for the application.

Motion free tomographic or multi-projection imaging eliminates mechanically induced artifacts in the sensitive detection system. It further eliminates the shock and vibration translated from mount to detector during the detector read, which may be conducted during mount movement in current systems.

For the present invention, exposure rate is not limited by the X-ray tube and mount movement time. Because the X-ray emission technology provides rapid generation at a plurality of flux angles, the system acquisition rate is primarily by exposure time and the detector readout. Unlike mechanically swept projection systems, exposure projection angle sequences are not necessarily required to be monotonic, and this generates another degree of freedom for advanced applications.

Another embodiment of the present invention includes a distributed set of X-ray sources 50-72 generating the projection images by electronically gating the emissions, rather than mechanically sweeping the mount. These X-ray sources 50-72 may be one of several technologies, for example field emission, spindt tips, electron gun, thermal emission filaments, etc.

Still another embodiment of the present invention includes a stationary pre-patient collimator 92 to align the output of each X-ray source 50-72 onto the detector 20. Generally, the collimator 92 is a device including a high absorption coefficient material used in collimation, wherein collimation is the operation of controlling a beam of radiation so that if the X-ray source were a point, the X-rays would become parallel.

Figure 3:
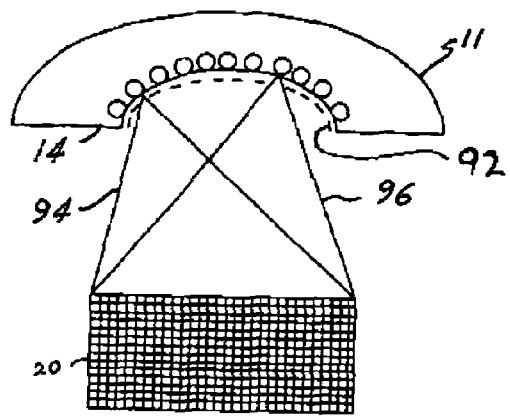
FIG. 3 is an operational diagram of a mammography scanning system according to another embodiment of the present invention.

Referring to FIG. 3, the X-ray sources 14 are activated by either a host computer 24 or an X-ray controller 28, as will be understood by one skilled in the art. The X-ray sources 14 send the X-ray flux 94, 96 through an object held by the mount 12 controlled by the mount control device 30 acting in response to signals from the host computer 24.

The X-ray flux 94, 96 from the X-ray sources 14 passes through the patient and impinges on the X-ray detector 20. The signal passes directly to the host computer 24 and display 26, where the signal is converted to a gray level corresponding to the attenuation of the X-ray photon through the patient, for the final image.

The present invention is illustrated with respect to mammography, however it is alternately used for any type of X-ray system using detectors including: computed tomography (CT), vascular X-ray imaging, bone scanning, etc. Further embodiments include non-medical applications such as weld inspection, metal inspection.

In operation, the host computer 24 receives the detector signals. The host computer 24 also activates the X-ray sources 14 either simultaneously or in succession, however, alternate embodiments include independent activation means for the X-ray sources 14. The present invention includes an operator console 25 for control by technicians, as will be understood by one skilled in the art.

Data is acquired and processed, and an image, for example, is presented to a radiology technician through the operator consol 25 while the scan is occurring. The host computer 24 needs only read the detector signals and up-date the display at the appropriate locations through, for example, an image reconstructor 36 and data acquisition system (DAS) 38. The host computer 24 alternately stores image data in a mass storage unit 34 for future reference.

While particular embodiments of the present invention have been shown and described, numerous variations and alternate embodiments will occur to those skilled in the art. Accordingly, it is intended that the invention be limited only in terms of the appended claims.

The invention claimed is:

1. A scanning system comprising:
a mount comprising a platform, wherein said mount further defines a holding area for supporting patient tissue;
a mount motor controller moving at least one of said mount or said platform vertically in response to adjustment signals,
a detector coupled to at least one of said mount or said platform and comprising a plurality of modules receiving a plurality of X-ray fluxes and generating detector signals therefrom;
at least three X-ray sources coupled to a support and arranged in an arc such that said at least three X-ray sources sequentially generate said plurality of X-ray signals for at least three different angles along said arc with respect to said detector; and
a computer generating said adjustment signals as a function of parameters of said patient tissue, said computer further generating an image signal as a function of said detector signals.

2. The system of claim 1, wherein said mount is arranged for a scanning procedure comprising at least one of mammography, computed tomography (CT), vascular X-ray imaging, or bone scanning.

3. The system of claim 1, further comprising at least one of a liquid cooling system, a common conditioner for said sources and said detector, or multiple chillers for said sources and said detector.

4. The system of claim 1, wherein said plurality of X-ray sources electronically gate said plurality of X-ray fluxes.

* * * * *